(12) United States Patent
Wang et al.

(10) Patent No.: US 11,577,228 B2
(45) Date of Patent: Feb. 14, 2023

(54) POROUS LAYERED TRANSITION METAL DICHALCOGENIDE AND PREPARATION METHOD AND USE THEREOF

(71) Applicant: Hangzhou Normal University, Zhejiang (CN)

(72) Inventors: Cheng Wang, Zhejiang (CN); Weiming Xu, Zhejiang (CN); Huilin Zheng, Zhejiang (CN); Pengfei Zhang, Zhejiang (CN); Hongyun Shen, Zhejiang (CN); Xiaoling Li, Zhejiang (CN)

(73) Assignee: HANGZHOU NORMAL UNIVERSITY, Zhejiang (CN)

( * ) Notice: Subject to any disclaimer, the term of this patent is extended or adjusted under 35 U.S.C. 154(b) by 0 days.

(21) Appl. No.: 16/931,716

(22) Filed: Jul. 17, 2020

(65) Prior Publication Data

US 2021/0362134 A1 Nov. 25, 2021

(30) Foreign Application Priority Data

May 20, 2020 (CN) .......................... 202010430303.2

(51) Int. Cl.
*B01J 27/057* (2006.01)
*B01J 35/00* (2006.01)
(Continued)

(52) U.S. Cl.
CPC ......... *B01J 27/0573* (2013.01); *B01J 35/004* (2013.01); *B01J 35/023* (2013.01);
(Continued)

(58) Field of Classification Search
CPC .. B01J 27/0573; B01J 27/0576; B01J 27/047; B01J 27/051; B01J 27/188; B01J 35/004;
(Continued)

(56) References Cited

U.S. PATENT DOCUMENTS

| 4,243,553 | A | * | 1/1981 | Naumann | .............. B01J 27/051 |
| | | | | | 423/53 |
| 4,243,554 | A | * | 1/1981 | Naumann | .............. B01J 27/051 |
| | | | | | 423/53 |

(Continued)

FOREIGN PATENT DOCUMENTS

| CN | 10 3910340 | * | 7/2014 | ............. B82Y 30/00 |
| CN | 10 8862387 | * | 11/2018 | ............ B01J 27/051 |
| CN | 11 1841579 | * | 10/2020 | ............ B01J 27/051 |

OTHER PUBLICATIONS

Yifeng Shi et al., "Highly Ordered Mesoporous Crystalline MoSe2 Material with Efficient Visible-Light-Driven PHotocatalytic Activity and Enhanced Lithium Storage Performance." Advanced Functional Materials, 23, pp. 1832-1838. (Year: 2013).*

(Continued)

*Primary Examiner* — Patricia L. Hailey
(74) *Attorney, Agent, or Firm* — W&G Law Group (57) ABSTRACT

The present invention relates to the field of catalysts, and provides a porous layered transition metal dichalcogenide (TMD) and a preparation method and use thereof. The preparation method includes the following steps: (1) mixing silica microspheres, a transition metal salt and an elemental chalcogen, and pressing to obtain a tablet, the silica microspheres having a same or different particle diameters; and (2) sintering the tablet under hydrogen, and removing the silica microspheres to obtain the porous layered TMD. The porous layered TMD prepared by the method of the present invention has a high lattice edge exposure, which provides more active sites and higher catalytic activity, so the porous layered TMD can effectively catalyze the oxidation of alcohols to aldehydes or sulfides to sulfoxides under visible light irradiation.

14 Claims, 2 Drawing Sheets

(51) Int. Cl.
*B01J 35/02* (2006.01)
*B01J 35/10* (2006.01)
*B01J 37/00* (2006.01)
*B01J 37/04* (2006.01)
*B01J 37/08* (2006.01)
*C07C 45/29* (2006.01)
*C07C 315/02* (2006.01)
*C07C 317/10* (2006.01)

(52) U.S. Cl.
CPC ........... *B01J 35/10* (2013.01); *B01J 37/0009* (2013.01); *B01J 37/04* (2013.01); *B01J 37/08* (2013.01); *C07C 45/29* (2013.01); *C07C 315/02* (2013.01); *C07C 317/10* (2013.01)

(58) Field of Classification Search
CPC ...... B01J 35/023; B01J 35/10; B01J 37/0009; B01J 37/04; B01J 37/08; C07C 45/29; C07C 315/02; C07C 317/10
USPC ............... 502/215, 216, 219, 220, 254, 255; 514/569
See application file for complete search history.

(56) References Cited

U.S. PATENT DOCUMENTS

| | | | | |
|---|---|---|---|---|
| 4,288,422 A * | 9/1981 | Chianelli | ............... | C01G 55/00 423/509 |
| 4,320,030 A * | 3/1982 | Happel | ................... | B01J 27/02 502/202 |
| 4,368,115 A * | 1/1983 | Chianelli | ................. | B01J 27/02 208/145 |
| 4,853,359 A * | 8/1989 | Morrison | ................. | B01J 27/04 502/220 |
| 10,414,668 B1 * | 9/2019 | Vaia | ....................... | C01G 33/00 |
| 2003/0130115 A1 * | 7/2003 | Rendina | ................. | B01J 27/047 502/219 |
| 2014/0371057 A1 * | 12/2014 | Serov | .................. | H01M 4/8605 502/174 |

OTHER PUBLICATIONS

Coehoorn, et al., "Electronic Structure of MOSe2, MoS2, and WSe2 . . . ," Physical Review B, vol. 35, No. 12, Univ. of Groningen, Apr. 1987.

Jaramillo, et al., "Identification of Active Edge Sites for Electrochemical H2 Evolution from MoS2 Nanocatalysts," Sciencevol. 317(5834):100-102, Jul. 6, 2007.

* cited by examiner

POROUS LAYERED TRANSITION METAL DICHALCOGENIDE AND PREPARATION METHOD AND USE THEREOF

CROSS REFERENCE TO RELATED APPLICATIONS

This application claims priority under 35 U.S.C. § 119(a) to Chinese patent application number 202010430303.2, filed on May 20, 2020, the entire teachings of which are incorporated herein by reference.

BACKGROUND OF THE INVENTION

Field of the Invention

The present invention relates to the field of catalysts, in particular to a porous layered transition metal dichalcogenide (TMD) and a preparation method and use thereof.

Description of the Related Art

Layered transition metal dichalcogenides (TMDs) are generally in the form of $MX_2$, where M is a transition metal atom, typically Mo, W and V, etc., and X is a chalcogen atom, such as S, Se and Te. TMDs have a layered lattice similar to graphite, which generally consists of three layers of atoms. Among them, the interlayer is a layer of transition metal atoms, and the two sandwich layers are layers of chalcogen atoms. The layered lattice is generally expressed as X-M-X, where the metal atoms and the chalcogen atoms each are combined by strong chemical bonds, and the lattice layers are stacked by weak van der Waals force. As a semiconductor, TMDs have a special energy band structure. In TMDs, electronic transition typically occurs in the d-orbital electrons of metal atoms rather than the valence electrons of chalcogen atoms, which greatly improves the photocorrosion resistance of S/Se/Te and the stability of the material (R. Coehoorn, C. Haas, J. Dijkstra, CJF Flipse, RAD Groot, A. Wold. Electronic Structure of $MoSe_2$, $MoS_2$, and $WSe_2$. I. Band-structure Calculations and Photoelectron Spectroscopy [J]. Phys. Rev. B, 1987, 35 (12), 6195-6202). In addition, due to the narrow band gap (<2.4 eV), TMDs are prone to photocatalytic reaction under visible light irradiation. However, for ordinary TMDs, since the atomic bonds in the lattice layers are saturated, there are few catalytic active sites, which leads to poor catalytic performance.

Studies have shown that the catalytic activity of the material is greatly improved if there are a large number of dangling bonds at the edge of the lattice. Theoretically, it is considered that the edge of the lattice is an active site for various catalytic reactions (T F Jaramillo, K P Jorgensen, J. Bonde, J H Nielsen, S. Horch, I. Chorkendorff. Identification of Active Edge Sites for Electrochemical $H_2$ Evolution from $MoS_2$ Nanocatalysts [J]. Science, 2007, 317, 100-102.). However, since the materials have a strong spontaneous tendency to reduce surface energy during the growth of crystals, TMDs always form lamellar topography or curl into nanotube topography, which reduces the lattice edge exposure. Therefore, in order to design and synthesize high-performance TMD catalysts with high lattice edge exposure, it is necessary to solve the key problem of the thermodynamic spontaneous tendency of the materials during crystal growth.

BRIEF SUMMARY OF THE INVENTION

The present invention provides a porous layered transition metal dichalcogenide (TMD) and a preparation method and use thereof. The porous layered TMD prepared by the method of the present invention has a high lattice edge exposure, which provides more active sites and higher catalytic activity, so the porous layered TMD can effectively catalyze the oxidation of alcohols to aldehydes or sulfides to sulfoxides under visible light irradiation.

The present invention provides a method for preparing a porous layered transition metal dichalcogenide (TMD), including the following steps:
1. mixing silica microspheres, a transition metal salt and an elemental chalcogen, and pressing to obtain a tablet, the silica microspheres having a same or different particle diameters; and
2. sintering the tablet under hydrogen, and removing the silica microspheres to obtain the porous layered TMD.

Preferably, in step (1), the silica microspheres have a diameter of 5-200 nm.

Preferably, in step (1), the transition metal salt includes one or two of phosphotungstic acid (PTA), ammonium metatungstate (AMT) and ammonium molybdate (AM).

Preferably, in step (1), the elemental chalcogen includes one or two of S, Se and Te.

Preferably, in step (1), a mass ratio of the silica microspheres to the transition metal salt is 1:(0.05-1), and a mass ratio of the silica microspheres to the elemental chalcogen is 1:(0.05-1).

Preferably, in step (2), the sintering is performed at 400-900° C. for 2-5 h.

Preferably, in step (2), the silica microspheres are removed by using a reagent including an aqueous solution of hydrofluoric acid, an aqueous solution of sodium hydroxide or an aqueous solution of potassium hydroxide; the aqueous solution of hydrofluoric acid has a mass concentration of 10-40%; the aqueous solution of sodium hydroxide has a mass concentration of 5-40%; the aqueous solution of potassium hydroxide has a mass concentration of 5-40%.

The present invention further provides a porous layered TMD prepared by the above preparation method.

The present invention further provides use of the porous layered TMD as a photocatalyst for a photocatalytic selective oxidation reaction, which includes the oxidation of an alcohol to an aldehyde or a sulfide to a sulfoxide.

Preferably, the oxidation of an alcohol to an aldehyde is specifically the oxidation of alkoxybenzyl alcohol to alkoxybenzaldehyde; the oxidation of a sulfide to a sulfoxide is specifically the oxidation of 5-fluoro-2-methyl-1-(4-thiobenzylidene)-3-indeneacetic acid to (Z)-5-fluoro-2-methyl-1-[[4-(methylsulfinyl)phenyl]methylene]-3-indenacetic acid.

Beneficial Effects

The present invention provides a porous layered TMD, including the following steps: (1) mixing silica microspheres, a transition metal salt and an elemental chalcogen, and pressing to obtain a tablet, the silica microspheres having a same or different particle diameters; and (2) sintering the tablet under hydrogen, and removing the silica microspheres to obtain the porous layered TMD. In the present invention, the silica microspheres with a same or different particle diameters are used as templates of the porous structure of the layered TMD. After the templates are removed, the adjustable pores of the catalyst increase, making it easy to adsorb molecules of various sizes, and improving the catalytic activity of the material. During the sintering process, the hydrogen reacts with the elemental chalcogen to produce a gas such as hydrogen sulfide, hydrogen selenide or hydrogen telluride. The generated gas reacts with the transition metal salt to spontaneously form a layered TMD, which includes the silica microspheres. After the silica microspheres are removed, all the positions originally occupied by the silica microspheres become voids, thus forming porous layered TMDs of various sizes. The porous structure increases the lattice edge exposure to provide more active sites. Therefore, the porous layered TMD of the present invention has high catalytic activity.

The results of the examples show that the porous layered TMDs of different sizes prepared by the method of the present invention have many active sites and high specific surface area.

In addition, the preparation method of the present invention has the advantage of simple steps.

The present invention further provides a porous layered TMD prepared by the preparation method as described in the above technical solution. The porous layered TMD prepared by the present invention has high specific area and many active sites, and thus can effectively catalyze the oxidation of alcohols to aldehydes or sulfides to sulfoxides. The results of the examples show that the specific surface area of the layered TMD is up to 29 m$^2$/g.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein.

DETAILED DESCRIPTION OF THE INVENTION

The present invention provides a porous layered transition metal dichalcogenide (TMD), including the following steps:
1. mix silica microspheres, a transition metal salt and an elemental chalcogen, and press to obtain a tablet; and
2. sinter the tablet under hydrogen, and remove the silica microspheres to obtain the porous layered TMD.

The present invention mixes silica microspheres, a transition metal salt and an elemental chalcogen to obtain a mixture. In the present invention, the silica microspheres have a same or different particle diameters. The silica microscpheres have a diameter of preferably 5-200 nm, more preferably 10-190 nm and most preferably 50-150 nm. When the silica microspheres have different particle diameters, the present invention has no special requirement for the ratio of the silica microspheres of different particle diameters, and those skilled in the art can select any ratio as needed. In the present invention, the transition metal salt preferably includes one or two of phosphotungstic acid (PTA), ammonium metatungstate (AMT) and ammonium molybdate (AM). When the transition metal salt includes two of these components, the present invention has no special requirement for the ratio of each transition metal salt, and any ratio can be used. The elemental chalcogen preferably includes one or two of S, Se and Te. When the elemental chalcogen includes two of these components, the present invention has no special requirement for the ratio of each elemental chalcogen, and any ratio can be used. In the present invention, the mass ratio of the silica microspheres to the transition metal salt is preferably 1:(0.05-1), more preferably 1:(0.06-1) and most preferably 1:(0.1-0.9). The mass ratio of the silica microspheres to the elemental chalcogen is preferably 1:(0.05-1), more preferably 1:(0.06-1) and most preferably 1:(0.1-0.9). In the present invention, the silica microspheres serve as templates of the porous structure of the porous layered TMD. When the silica microspheres of different particle diameters are used as the templates, the adjustable pores of the catalyst increase, making it easy to adsorb molecules of various sizes, and improving the catalytic activity of the material.

In the present invention, the mixing is preferably realized by grinding. The present invention has no special limit on the grinding process and fineness as long as all raw materials are mixed evenly without large particles visible to the naked eye.

After obtaining the mixture, the present invention presses the mixture to obtain a tablet. In the present invention, the pressing is performed under a pressure of preferably 20-45 Mpa, more preferably 25-40 Mpa and most preferably 30-35 Mpa. In the present invention, the mixture is shaped by pressing, which is beneficial to form the porous layered TMD through the subsequent sintering treatment.

After obtaining the tablet, the present invention sinters the tablet under hydrogen to obtain a layered TMD including the silica microspheres.

In the present invention, the sintering is performed at a temperature of preferably 400-900° C., more preferably 450-850° C. and most preferably 500-800° C. for a time of preferably 2-5 h, more preferably 2.5-4.5 h and most preferably 3-4 h. In the present invention, the sintering is performed under hydrogen, which has a flow rate of preferably 100-500 mL/min, more preferably 150-450 mL/min and most preferably 200-400 mL/min.

In the present invention, during the sintering process, the hydrogen first reacts with the elemental chalcogen to produce a gas such as hydrogen sulfide, hydrogen selenide or hydrogen telluride. Then to reduce Gibbs free energy (GFE), the generated gas reacts with the transition metal salt to spontaneously form a layered TMD including the silica microspheres.

After the sintering reaction is completed, the present invention preferably cools a sintered product down to obtain a layered TMD including the silica microspheres. The present invention has no special requirement for the specific cooling method, and a cooling method well known to those skilled in the art can be used. In the present invention, the sintered product is preferably cooled down to 20-30° C.

After obtaining the layered TMD with the silica microspheres, the present invention removes the silica microspheres to obtain the porous layered TMD.

In the present invention, the silica microspheres are preferably removed by using a reagent including an aqueous solution of hydrofluoric acid, an aqueous solution of sodium hydroxide or an aqueous solution of potassium hydroxide. The aqueous solution of hydrofluoric acid has a mass concentration of preferably 10-40%, and more preferably 15-35%. The aqueous solution of sodium hydroxide has a mass concentration of preferably 5-40%, and more preferably 10-35%. The aqueous solution of potassium hydroxide has a mass concentration of 5-40%, more preferably 10-35%.

In the present invention, the silica microspheres are preferably removed as follows: mix the layered TMD including the silica microspheres with the above-mentioned reagent; stir at room temperature; filter to obtain a solid; and dry the obtained solid. The present invention has no special requirement for the amount of the reagent and the condition of the stirring for removing the silica microspheres, as long as the silica microspheres can be completely removed.

After the silica microspheres are removed, all the positions originally occupied by the silica microspheres become voids, thus forming the porous layered TMD. The porous structure increases the lattice edge exposure to provide more active sites. Therefore, the porous layered TMD of the present invention has high catalytic activity.

The present invention further provides a porous layered TMD prepared by the preparation method as described in the above-mentioned technical solution. In the present invention, the porous layered TMD is a nano-scale two-dimensional (2D) porous layered structure, which has a pore size of preferably 5-200 nm, more preferably 10-190 nm and most preferably 50-150 nm. The porous layered TMD prepared by the present invention has a high specific area (up to 29 m$^2$/g) and many active sites, and thus can effectively catalyze the oxidation of alcohols to aldehydes or sulfides to sulfoxides.

The present invention further provides use of the porous layered TMD in the above technical solution as a photocatalyst for a photocatalytic selective oxidation reaction, which includes the oxidation of an alcohol to an aldehyde or a sulfide to a sulfoxide.

In the present invention, the oxidation of an alcohol to an aldehyde is preferably the oxidation of alkoxybenzyl alcohol to alkoxybenzaldehyde; the oxidation of a sulfide to a sulfoxide is preferably the oxidation of 5-fluoro-2-methyl-1-(4-thiobenzylidene)-3-indeneacetic acid to (Z)-5-fluoro-2-methyl-1-[[4-(methylsulfinyl)phenyl]methylene]-3-indenacetic acid (also known as sulindac).

In the present invention, the oxidation of alkoxybenzyl alcohol to alkoxybenzaldehyde by the porous layered TMD as a catalyst under visible light irradiation is preferably:

mix the alkoxybenzyl alcohol, the porous layered TMD and an organic solvent for a photocatalytic reaction under visible light irradiation to yield alkoxybenzaldehyde.

In the present invention, the organic solvent preferably includes one or more of acetonitrile, toluene and cyclohexane, more preferably acetonitrile. In the present invention, the mass ratio of the alkoxybenzyl alcohol to the porous layered TMD is preferably 1:(0.001-0.02), more preferably 1:(0.002-0.02) and most preferably 1:(0.005-0.18). In the present invention, the mass ratio of the alkoxybenzyl alcohol to the organic solvent is preferably 1:(2-10), more preferably 1:(3-9) and most preferably 1:(4-8).

In the present invention, the visible light is preferably mixed visible light in the 380-780 nm band.

In the present invention, the photocatalytic reaction is preferably carried out in a quartz reaction vessel.

In the present invention, the photocatalytic reaction is carried out at a temperature of preferably 20-80° C., more preferably 30-70° C. and most preferably 40-60° C. for a time of preferably 2-12 h, more preferably 4-10 h and most preferably 5-8 h.

After the photocatalytic reaction is completed, the alkoxybenzaldehyde exists in the reaction product system in a liquid form. The present invention preferably filters the reaction product system to recover the catalyst and distill the filtrate to recover the reaction solvent after the photocatalytic reaction. During the distillation, the alkoxybenzaldehyde is precipitated as a solid. The present invention preferably filters a system remaining after rotary evaporation, and recrystallizes the filter cake to obtain alkoxybenzaldehyde. The recrystallization preferably uses petroleum ether as a solvent.

In the present invention, the oxidation of alkoxybenzyl alcohol to alkoxybenzaldehyde by the porous layered TMD is expressed as Formula I:

Formula I

One of the substituents of R1 and R2 is methoxy or benzyloxy, and the other is methyl, hydrogen or hydroxy.

In the present invention, the oxidation of 5-fluoro-2-methyl-1-(4-thiobenzylidene)-3-indeneacetic acid to sulindac by the above porous layered TMD under visible light irradiation is preferably:

mix the 5-fluoro-2-methyl-1-(4-thiobenzylidene)-3-indeneacetic acid, the porous layered TMD and an organic solvent for a photocatalytic reaction under visible light irradiation to yield sulindac.

In the present invention, the organic solvent preferably includes one or more of acetonitrile, toluene and cyclohexane, more preferably acetonitrile. In the present invention, the mass ratio of the 5-fluoro-2-methyl-1-(4-thiobenzylidene)-3-indeneacetic acid to the porous layered TMD is preferably 1:(0.002-0.02), more preferably 1:(0.004-0.02) and most preferably 1:(0.01-0.18). In the present invention, the mass ratio of the alkoxybenzyl alcohol to the organic solvent is preferably 1:(2-10), more preferably 1:(3-9) and most preferably 1:(4-8).

In the present invention, the visible light is preferably mixed visible light in the 380-780 nm band.

In the present invention, the photocatalytic reaction is preferably carried out in a quartz reaction vessel.

In the present invention, the photocatalytic reaction is carried out at a temperature of preferably 20-80° C., more preferably 30-70° C. and most preferably 40-60° C. for a time of preferably 2-12 h, more preferably 4-10 h and most preferably 5-8 h.

After the photocatalytic reaction is completed, the sulindac exists in the reaction product system in a liquid form. The present invention preferably filters the reaction product system to recover the catalyst and distill the filtrate to recover the reaction solvent after the photocatalytic reaction. During the distillation, the sulindac is precipitated as a solid.

The present invention preferably filters a system remaining after rotary evaporation, and recrystallizes the filter cake to obtain sulindac. The recrystallization preferably uses isopropanol as a solvent.

In the present invention, the oxidation of 5-fluoro-2-methyl-1-(4-thiobenzylidene)-3-indeneacetic acid to sulindac by the layered TMD is expressed as Formula II:

The technical solution of the present invention is clearly and completely described below with reference to the examples of the present invention.

Example 1

20 g of $SiO_2$ microspheres with a diameter of 200 nm, 20 g of AMT and 20 g of selenium powder were fully ground and mixed, and 60 g of the mixed powder was pressed under 45 Mpa into a tablet by a tablet press.

The obtained tablet was sintered with hydrogen with a flow rate of 200 mL/min in a tube furnace at 700° C. for 2 h. After the reaction was completed, a sintered product was cooled to room temperature, and then added into 450 mL of aqueous solution of hydrofluoric acid with a mass concentration of 10%. The reactant was stirred at 25° C. for 2 h. After the reaction was completed, the solution was filtered to obtain a solid. The solid was dried to obtain 27.58 g of $WSe_2$ having a porous layered structure with a specific surface area of 9 $m^2/g$.

Figure 1:
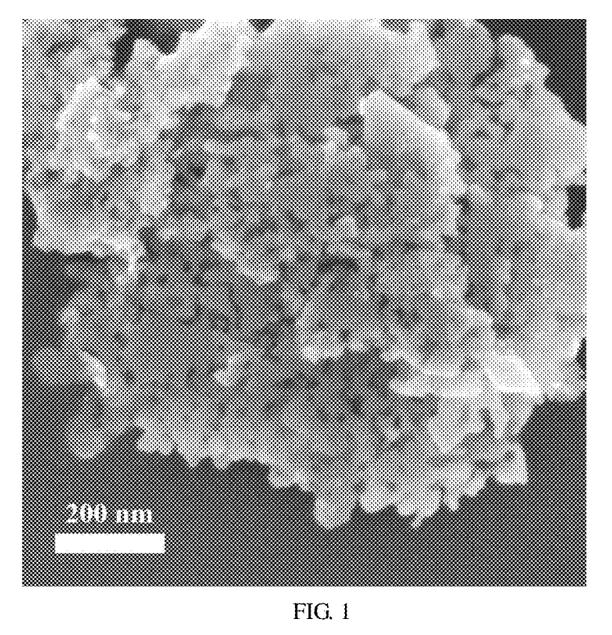
FIG. 1 is an image (taken by a scanning electron microscope, SEM) of WSe$_2$ prepared by Example 1.

FIG. 1 shows an image (taken by a scanning electron microscope, SEM) of the catalyst $WSe_2$ obtained in Example 1. FIG. 1 indicates that $WSe_2$ has a regular structure, which is a nano-scale 2D porous layered structure. It can be intuitively seen from the characterization that the porous structure increases the edge area, thereby greatly improving the lattice edge exposure. In addition, the SEM image indicates that the layers of the material do not intersect but stack, which ensures high lattice edge exposure.

Example 2

20 g of $SiO_2$ microspheres with a diameter of 5 nm, 1 g of AMT and 1 g of selenium powder were fully ground and mixed, and 22 g of the mixed powder was pressed under 30 Mpa into a tablet by a tablet press.

The obtained tablet was sintered with hydrogen with a flow rate of 200 mL/min in a tube furnace at 700° C. for 2 h. After the reaction was completed, a sintered product was cooled to room temperature, and then added into 120 mL of aqueous solution of hydrofluoric acid with a mass concentration of 40%. The reactant was stirred at 25° C. for 2 h. After the reaction was completed, the solution was filtered to obtain a solid. The solid was dried to obtain 1.38 g of $WSe_2$ having a porous layered structure with a specific surface area of 29 $m^2/g$.

Example 3

2 g of $SiO_2$ microspheres with a diameter of 60 nm, 18 g of $SiO_2$ microspheres with a diameter of 15 nm, 5 g of AM and 5 g of selenium powder were fully ground and mixed, and 30 g of the mixed powder was pressed under 20 Mpa into a tablet by a tablet press.

The obtained tablet was sintered with hydrogen with a flow rate of 200 mL/min in a tube furnace at 700° C. for 2 h. After the reaction was completed, a sintered product was cooled to room temperature, and then added into 150 mL of aqueous solution of hydrofluoric acid with a mass concentration of 30%. The reactant was stirred at 25° C. for 2 h. After the reaction was completed, the solution was filtered to obtain a solid. The solid was dried to obtain 6.48 g of $MoSe_2$ having a porous layered structure with a specific surface area of 19 $m^2/g$.

Figure 2:
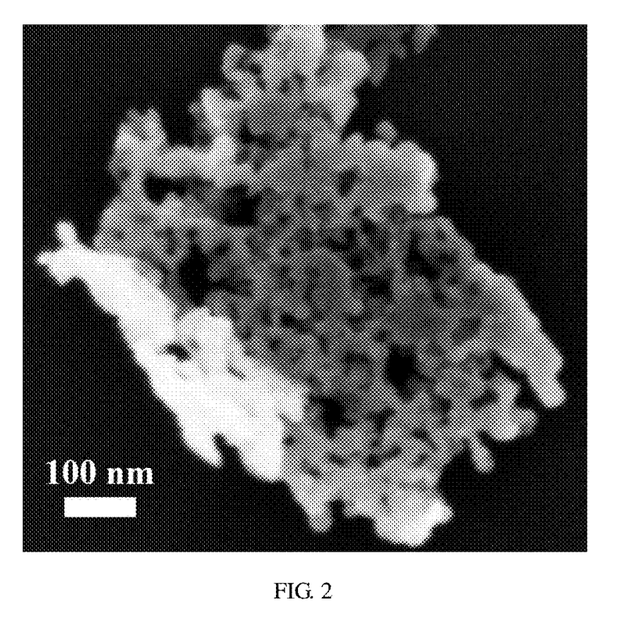
FIG. 2 is an SEM image of MoSe$_2$ prepared by Example 3.
Figure 3:
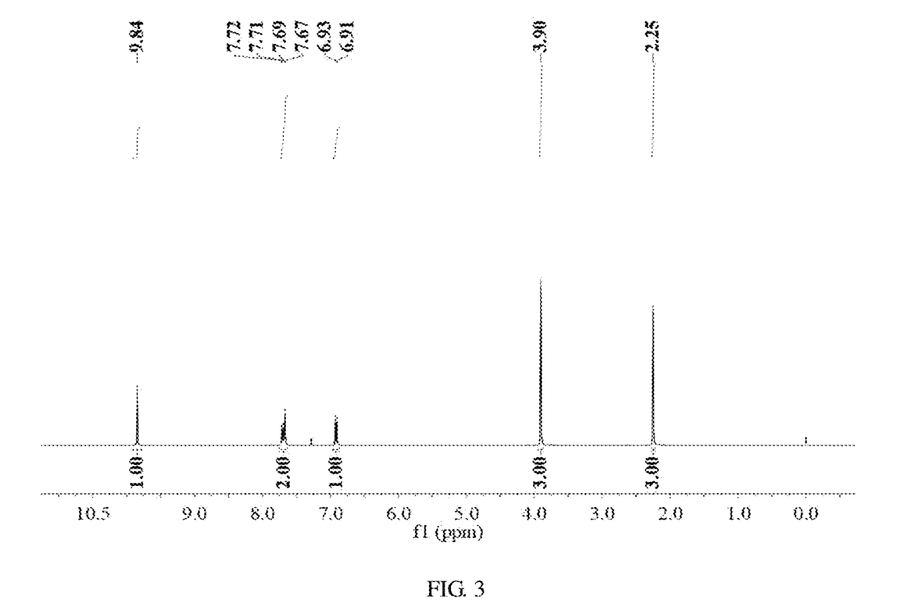
FIG. 3 is a spectrum of p-3-methyl-4-methoxybenzaldehyde prepared in Application Example 3, obtained by hydrogen-1 nuclear magnetic resonance ($^1$H NMR) spectroscopy.

FIG. 3 shows an SEM image of the catalyst $MoSe_2$ obtained in Example 3. FIG. 2 indicates that $MoSe_2$ has a regular structure, which is a nano-scale 2D porous layered structure. It can be intuitively seen from the characterization that the porous structure increases the edge area, thereby greatly improving the lattice edge exposure. In addition, because two $SiO_2$ microspheres of different diameters were used, the generated catalyst $MoSe_2$ had pores of different sizes, which was conducive to the catalytic reaction and ensured high lattice edge exposure.

Example 4

20 g of $SiO_2$ microspheres with a diameter of 100 nm, 10 g of AM and 10 g of selenium powder were fully ground and mixed, and 40 g of the mixed powder was pressed under 40 Mpa into a tablet by a tablet press.

The obtained tablet was sintered with hydrogen with a flow rate of 200 mL/min in a tube furnace at 700° C. for 2 h. After the reaction was completed, a sintered product was cooled to room temperature, and then added into 150 mL of aqueous solution of hydrofluoric acid with a mass concentration of 30%. The reactant was stirred at 25° C. for 2 h. After the reaction was completed, the solution was filtered to obtain a solid. The solid was dried to obtain 12.95 g of $MoSe_2$ having a porous layered structure with a specific surface area of 15 m²/g.

Example 5

10 g of $SiO_2$ microspheres with a diameter of 10 nm, 5 g of $SiO_2$ microspheres with a diameter of 60 nm, 5 g of $SiO_2$ microspheres with a diameter of 100 nm, 10 g of PTA and 15 g of selenium powder were fully ground and mixed, and 45 g of the mixed powder was pressed under 30 Mpa into a tablet by a tablet press.

The obtained tablet was sintered with hydrogen with a flow rate of 200 mL/min in a tube furnace at 700° C. for 2 h. After the reaction was completed, a sintered product was cooled to room temperature, and then added into 100 mL of aqueous solution of potassium hydroxide with a mass concentration of 40%. The reactant was stirred at 25° C. for 2 h. After the reaction was completed, the solution was filtered to obtain a solid. The solid was dried to obtain 18.29 g of $WTe_2$ having a porous layered structure with a specific surface area of 25 m²/g.

Example 6

10 g of $SiO_2$ microspheres with a diameter of 150 nm, 10 g of $SiO_2$ microspheres with a diameter of 50 nm, 5 g of AM and 5 g of selenium powder were fully ground and mixed, and 30 g of the mixed powder was pressed under 40 Mpa into a tablet by a tablet press.

The obtained tablet was sintered with hydrogen with a flow rate of 200 mL/min in a tube furnace at 700° C. for 2 h. After the reaction was completed, a sintered product was cooled to room temperature, and then added into 600 mL of aqueous solution of sodium hydroxide with a mass concentration of 5%. The reactant was stirred at 25° C. for 2 h. After the reaction was completed, the solution was filtered to obtain a solid. The solid was dried to obtain 6.48 g of $MoSe_2$ having a porous layered structure with a specific surface area of 12 m²/g.

Example 7

20 g of $SiO_2$ microspheres with a diameter of 100 nm, 14.08 g of AM, 5.92 g of AMT and 20 g of selenium powder were fully ground and mixed, and 60 g of the mixed powder was pressed under 30 Mpa into a tablet by a tablet press.

The obtained tablet was sintered with hydrogen with a flow rate of 200 mL/min in a tube furnace at 700° C. for 2 h. After the reaction was completed, a sintered product was cooled to room temperature, and then added into 150 mL of aqueous solution of hydrofluoric acid with a mass concentration of 30%. The reactant was stirred at 25° C. for 2 h. After the reaction was completed, the solution was filtered to obtain a solid. The solid was dried to obtain 26.37 g of $Mo_3WSe_8$ having a porous layered structure with a specific surface area of 15 m²/g.

Example 8

20 g of $SiO_2$ microspheres with a diameter of 100 nm, 20 g of AM, 2.18 g of elemental sulfur and 10.75 g of selenium powder were fully ground and mixed, and 52.93 g of the mixed powder was pressed under 30 Mpa into a tablet by a tablet press.

The obtained tablet was sintered with hydrogen with a flow rate of 200 mL/min in a tube furnace at 700° C. for 2 h. After the reaction was completed, a sintered product was cooled to room temperature, and then added into 150 mL of aqueous solution of hydrofluoric acid with a mass concentration of 30%. The reactant was stirred at 25° C. for 2 h. After the reaction was completed, the solution was filtered to obtain a solid. The solid was dried to obtain 22.72 g of $Mo_3S_2Se_4$ having a porous layered structure with a specific surface area of 15 m²/g.

Application Example 1

100 g of p-methoxybenzyl alcohol was added into a reaction vessel to dissolve in 200 g of acetonitrile. Then 0.1 g of the catalyst $WSe_2$ prepared in Example 1 was added. The reaction was performed at 80° C. for 2 h under visible light irradiation. After the reaction was completed, the solution was filtered to recover the catalyst, and the filtrate was distilled to recover the solvent, thus obtaining 96.6 g of target product, i.e. p-methoxybenzaldehyde, with a yield of 98.0%. Hydrogen-1 nuclear magnetic resonance: $^1H$ NMR (500 MHz, $CDCl_3$) δ 9.88 (s, 1H), 7.92-7.75 (m, 2H), 7.08-6.91 (m, 2H), 3.89 (s, 3H).

Application Example 2

100 g of p-benzyloxybenzyl alcohol was added into a reaction vessel to dissolve in 300 g of toluene. Then 2 g of the catalyst $WTe_2$ prepared in Example 5 was added. The reaction was performed at 20° C. for 12 h under visible light irradiation. After the reaction was completed, the solution was filtered to recover the catalyst, and the filtrate was distilled to recover the solvent. The system obtained after distillation was filtered, and the filter cake was recrystallized with petroleum ether to obtain 94.5 g of p-benzyloxybenzaldehyde with a yield of 95.4%.

Application Example 3

100 g of 3-methyl-4-methoxybenzyl alcohol was added into a reaction vessel to dissolve in 300 g of toluene. Then 1 g of the catalyst $MoSe_2$ prepared in Example 4 was added. The reaction was performed at 35° C. for 8 h under visible light irradiation. After the reaction was completed, the solution was filtered to recover the catalyst, and the filtrate was distilled to recover the solvent. The system after the distillation was filtered, and the filter cake was recrystallized with petroleum ether to obtain 96.6 g of p-3-methyl-4-methoxybenzaldehyde with a yield of 97.9%. Hydrogen-1 nuclear magnetic resonance: $^1H$ NMR (400 MHz, $CDCl_3$) δ 9.84 (s, 1H), 7.76-7.62 (m, 2H), 6.92 (d, J=8.4 Hz, 1H), 3.90 (s, 3H), 2.25 (s, 3H), as shown in FIG. 3.

Application Example 4

100 g of 3-hydroxy-4-methoxybenzyl alcohol was added into a reaction vessel to dissolve in 300 g of cyclohexane. Then 1 g of the catalyst $Mo_3S_2Se_4$ prepared in Example 8 was added. The reaction was performed at 30° C. for 6 h under visible light irradiation. After the reaction was completed, the solution was filtered to recover the catalyst, and the filtrate was distilled to recover the solvent. The system after the distillation was filtered, and the filter cake was recrystallized with petroleum ether to obtain 96.9 g of p-3-hydroxy-4-methoxybenzaldehyde with a yield of 98.2%. Hydrogen-1 nuclear magnetic resonance: $^1H$ NMR (500 MHz, CDCl$_3$) δ 9.75 (s, 1H), 7.38-7.32 (m, 2H), 6.89 (d, J=8.1 Hz, 1H), 5.99 (s, 1H), 3.89 (s, 3H).

Application Example 5

Figure 4:
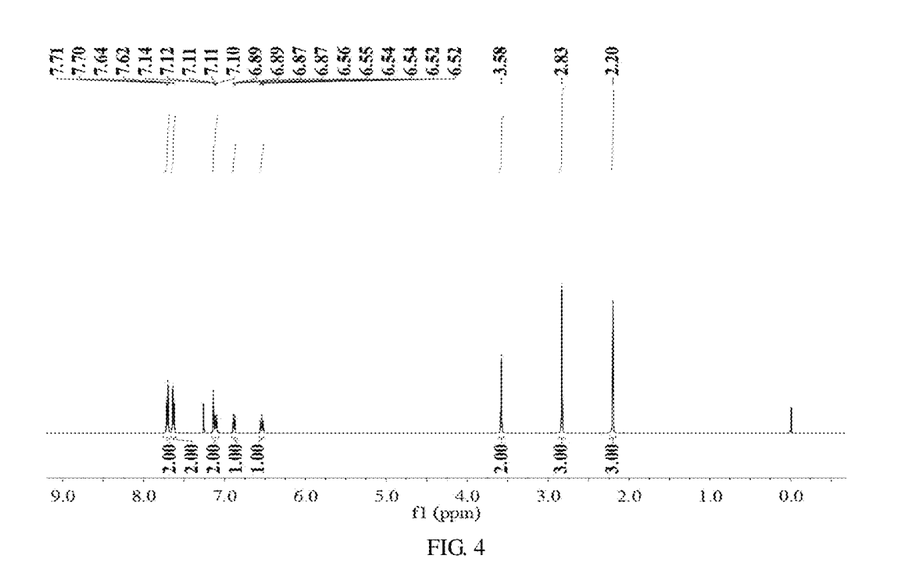
FIG. 4 is a spectrum of sulindac prepared in Application Example 5, obtained by $^1$H NMR spectroscopy.

100 g of 5-fluoro-2-methyl-1-(4-thiobenzylidene)-3-indeneacetic acid was added into a reaction vessel to dissolve in 200 g of toluene. Then 2 g of the catalyst MoSe$_2$ prepared in Example 3 was added. The reaction was performed at 20° C. for 12 h under visible light irradiation. After the reaction was completed, the solution was filtered to recover the catalyst, and the filtrate was distilled to recover the solvent. The system after the distillation was filtered, and the filter cake was recrystallized with isopropanol to obtain 99.6 g of sulindac with a yield of 95.1%. Hydrogen-1 nuclear magnetic resonance: $^1$H NMR (500 MHz, CDCl$_3$) δ 7.71 (d, J=8.1 Hz, 2H), 7.63 (d, J=8.2 Hz, 2H), 7.17-7.07 (m, 2H), 6.88 (dd, J=8.8, 2.2 Hz, 1H), 6.54 (td, J=8.8, 2.2 Hz, 1H), 3.58 (s, 2H), 2.83 (s, 3H), 2.20 (s, 3H), as shown in FIG. 4.

Application Example 6

100 g of 5-fluoro-2-methyl-1-(4-thiobenzylidene)-3-indeneacetic acid was added into a reaction vessel to dissolve in 1,000 g of cyclohexane. Then 0.1 g of the catalyst WSe$_2$ prepared in Example 2 was added. The reaction was performed at 80° C. for 2 h under visible light irradiation. After the reaction was completed, the solution was filtered to recover the catalyst, and the filtrate was distilled to recover the solvent. The system after the distillation was filtered, and the filter cake was recrystallized with isopropanol to obtain 101.1 g of sulindac with a yield of 96.5%.

Application Example 7

100 g of 5-fluoro-2-methyl-1-(4-thiobenzylidene)-3-indeneacetic acid was added into a reaction vessel to dissolve in 500 g of acetonitrile. Then 0.5 g of the catalyst Mo$_3$WSe$_8$ prepared in Example 7 was added. The reaction was performed at 40° C. for 8 h under visible light irradiation. After the reaction was completed, the solution was filtered to recover the catalyst, and the filtrate was distilled to recover the solvent. The system after the distillation was filtered, and the filter cake was recrystallized with isopropanol to obtain 103.2 g of sulindac with a yield of 98.6%.

Comparative Example

The comparative example differs from Application Example 1 in that the catalyst was traditional non-porous WSe$_2$ (99.8%, Aladdin), and the rest were the same as those in Application Example 1. Finally, 39.6 g of target product, i.e. p-methoxybenzaldehyde was obtained with a yield of 40.2%. This indicates that the porous layered TMD prepared by the method of the present invention has higher catalytic activity.

Overall, the present invention provides a porous layered TMD and a preparation method and use thereof. The porous layered TMD prepared by the method of the present invention has a high lattice edge exposure, which provides more active sites and higher catalytic activity, so the porous layered TMD can effectively catalyze the oxidation of alcohols to aldehydes or sulfides to sulfoxides under visible light irradiation.

The above described are merely preferred implementations of the present invention. It should be noted that a person of ordinary skill in the art may further make several improvements and modifications without departing from the principle of the present invention, but such improvements and modifications shall also be deemed as falling within the protection scope of the present invention.

Having thus described the invention of the present application in detail and by reference to embodiments thereof, it will be apparent that modifications and variations are possible without departing from the scope of the invention defined in the appended claims as follows:

What is claimed is:

1. A method for preparing a porous layered transition metal dichalcogenide (TMD), comprising the following steps:
   (1) mixing silica microspheres, a transition metal salt and an elemental chalcogen, and pressing to obtain a tablet, the silica microspheres having a same or different particle diameters; and
   (2) sintering the tablet under hydrogen, and removing the silica microspheres to obtain the porous layered TMD, wherein, a mass ratio of the silica microspheres to the transition metal salt is 1:(0.05-1), and a mass ratio of the silica microspheres to the elemental chalcogen is 1:(0.05-1).

2. The preparation method according to claim 1, wherein in step (1), the silica microspheres have a diameter of 5-200 nm.

3. A porous layered TMD prepared by the preparation method according to claim 2.

4. The preparation method according to claim 1, wherein in step (1), the transition metal salt comprises one or two of phosphotungstic acid (PTA), ammonium metatungstate (AMT) and ammonium molybdate (AM).

5. A porous layered TMD prepared by the preparation method according to claim 4.

6. The preparation method according to claim 1, wherein in step (1), the elemental chalcogen comprises one or two of S, Se and Te.

7. A porous layered TMD prepared by the preparation method according to claim 6.

8. The preparation method according to claim 1, wherein in step (2), the sintering is performed at 400-900° C. for 2-5 h.

9. A porous layered TMD prepared by the preparation method according to claim 8.

10. The preparation method according to claim 1, wherein in step (2), the silica microspheres are removed by using a reagent comprising an aqueous solution of hydrofluoric acid, an aqueous solution of sodium hydroxide or an aqueous solution of potassium hydroxide; the aqueous solution of hydrofluoric acid has a mass concentration of 10-40%; the aqueous solution of sodium hydroxide has a mass concentration of 5-40%; the aqueous solution of potassium hydroxide has a mass concentration of 5-40%.

11. A porous layered TMD prepared by the preparation method according to claim 10.

12. A porous layered TMD prepared by the preparation method according to claim 1.

13. Use of the porous layered TMD according to claim 12 as a photocatalyst for a photocatalytic selective oxidation reaction, which comprises the oxidation of an alcohol to an aldehyde or a sulfide to a sulfoxide.

14. The use according to claim 13, wherein the oxidation of an alcohol to an aldehyde is specifically the oxidation of alkoxybenzyl alcohol to alkoxybenzaldehyde; the oxidation of a sulfide to a sulfoxide is specifically the oxidation of 5-fluoro-2-methyl-1-(4-thiobenzylidene)-3-indeneacetic acid to (Z)-5-fluoro-2-methyl-1-[[4-(methylsulfinyl)phenyl]methylene]-3-indenacetic acid.

\* \* \* \* \*